(12) United States Patent
Grokop et al.

(10) Patent No.: US 8,930,300 B2
(45) Date of Patent: Jan. 6, 2015

(54) SYSTEMS, METHODS, AND APPARATUSES FOR CLASSIFYING USER ACTIVITY USING TEMPORAL COMBINING IN A MOBILE DEVICE

(75) Inventors: Leonard Henry Grokop, San Diego, CA (US); Anthony Sarah, San Diego, CA (US); Sanjiv Nanda, Ramona, CA (US)

(73) Assignee: QUALCOMM Incorporated, San Diego, CA (US)

( * ) Notice: Subject to any disclaimer, the term of this patent is extended or adjusted under 35 U.S.C. 154(b) by 238 days.

(21) Appl. No.: 13/362,893

(22) Filed: Jan. 31, 2012

(65) Prior Publication Data

US 2012/0254100 A1    Oct. 4, 2012

Related U.S. Application Data

(60) Provisional application No. 61/470,016, filed on Mar. 31, 2011.

(51) Int. Cl.
| | | |
|---|---|---|
| *A61B 5/11* | (2006.01) | |
| *G06K 9/00* | (2006.01) | |
| *G06K 9/62* | (2006.01) | |
| *G06N 7/00* | (2006.01) | |

(52) U.S. Cl.
CPC .............. *A61B 5/1123* (2013.01); *G06N 7/00* (2013.01); *G06N 7/005* (2013.01); *G06K 9/00348* (2013.01); *G06K 9/00536* (2013.01); *G06K 9/6288* (2013.01)
USPC ............................................. 706/52; 706/45

(58) Field of Classification Search
USPC .................................................... 706/52, 45
See application file for complete search history.

(56) References Cited

U.S. PATENT DOCUMENTS 6,145,389 A    11/2000  Ebeling et al.
6,582,380 B2    6/2003  Kazlausky et al.
(Continued)

FOREIGN PATENT DOCUMENTS

JP    2010515175 A    5/2010
JP    2011504331 A    2/2011
(Continued)

OTHER PUBLICATIONS

Boyd, et al., Power-Accuracy Tradeoffs in Human Activity Transition Detection, Design, Automation & Test in Europe Conference & Exhibition (DATE), Mar. 8-12, 2010, pp. 1524-1529.*

(Continued)

*Primary Examiner* — Wilbert L Starks
(74) *Attorney, Agent, or Firm* — Kilpatrick Townsend & Stockton LLP

(57) ABSTRACT

Components, methods, and apparatuses are provided for determining activity likelihood function values for an activity classification for two or more past epochs based, at least in part, on signals from one or more sensors of a mobile device. A method may comprise, for each of a plurality of activity classifications, determining activity likelihood function values for each of the plurality of activity classifications for two or more past epochs. The activity likelihood function values may be based on signals from one or more sensors of a mobile device. The method may also include combining the activity likelihood function values to determine a likelihood function for an activity classification at a present epoch. The method may also include inferring a present activity of a user co-located with the mobile device to be one of the activity classifications based on the determined likelihood functions for the activity classifications at the present epoch.

27 Claims, 4 Drawing Sheets

(56) References Cited

U.S. PATENT DOCUMENTS

| | | |
|---|---|---|
| 7,881,902 B1 | 2/2011 | Kahn et al. |
| 2007/0006098 A1 | 1/2007 | Krumm et al. |
| 2009/0082699 A1 | 3/2009 | Bang et al. |
| 2009/0132197 A1 | 5/2009 | Rubin et al. |
| 2011/0313956 A1 | 12/2011 | Abe et al. |

FOREIGN PATENT DOCUMENTS

| | | |
|---|---|---|
| JP | 2012003494 A | 1/2012 |
| WO | WO-2008083320 A2 | 7/2008 |
| WO | WO-2009062176 A2 | 5/2009 |

OTHER PUBLICATIONS

Sperry, Analysis of Acoustic Propagation in the Region of the New England Continental Shelfbreak, Doctoral Dissertation, Massachusetts Institute of Technology, Woods Hole Oceanographic Institution, MIT/WHOI 99-09, 1999, pp. 1-183.*

International Search Report and Written Opinion—PCT/US2012/031697, International Search Authority—European Patent Office, Jul. 17, 2012.

Muscillo R et al., "An Adaptive Kalman-Based Bayes Estimation Technique to Classify Locomotor activities in young and elderly adults through accelerometers", Medical Engineering & Physics, Butterworth-Heinemann, GB, vol. 32, No. 8, Oct. 1, 2010, pp. 849-859, XP027267622, ISSN: 1350-4533 [retrieved on Jun. 23, 2010] paragraphs [2.1.1], [03.3].

Rowlands et al., "The Effect of Accelerometer EPOCH Onphysical Activity Output Measures", Journal of Exercise Science & Fitness, vol. 4, No. 1, 2006, XP7920771,Retrieved from the Internet: URL: http://www.scsepf.org/doc/210606/JESFO401-06.pdf, [retrieved on Jun. 29, 2012].

* cited by examiner

SYSTEMS, METHODS, AND APPARATUSES FOR CLASSIFYING USER ACTIVITY USING TEMPORAL COMBINING IN A MOBILE DEVICE

CROSS REFERENCE TO RELATED APPLICATIONS

The present application claims priority to U.S. provisional application No. 61/470,016, titled "Classification of User Activity Using Temporal Combining," filed Mar. 31, 2011, which is hereby incorporated by reference in its entirety.

BACKGROUND

1. Field

The subject matter disclosed herein relates to classifying user activity in a mobile device.

2. Information

Many mobile communication devices, such as smart-phones, include an inertial sensor, such as an accelerometer, that may be used to detect motion of the device. These movements may be useful in determining the device's orientation so that a display may be properly oriented, for example in a portrait or a landscape mode, when displaying information to a user. In another example, a gaming application performed by way of a smartphone may rely on movements detected by one or more accelerometers so that a feature of the game may be controlled. In other examples, a gesturing movement detected by an accelerometer may allow a user to scroll a map, navigate a menu, or control other aspects of the device's operation.

Though useful in assisting with simple user interface tasks, it has not been possible to make use of the output signals or "traces" of an accelerometer to provide more sophisticated and meaningful assistance to mobile device users. For example, if it can be detected that a user is engaged in a strenuous activity, it may be useful to direct incoming telephone calls immediately to voicemail so as not to distract the user. In another example, if it can be detected that a mobile device is in a user's purse or pocket, it may be advantageous to disable a display so as not to waste battery resources.

When attempting to infer user activity, such as walking, running, cycling, and so forth, various techniques may be used to acquire a signal from an inertial sensor, extract features from the acquired signal, and infer an activity class. However, when estimating a user's activity class, a trade-off may be made between performing an accurate estimation of a user's activity and performing the estimation in a timely manner. In general, accurate estimations may be available, but only after a processing delay.

SUMMARY

In a particular implementation, a method comprises, for each of a plurality of activity classifications, determining activity likelihood function values for each of the plurality of activity classifications for two or more past epochs. The activity likelihood function values are based, at least in part, on signals from one or more sensors of a mobile device. The method also includes combining the activity likelihood function values to determine a likelihood function for an activity classification at a present epoch. The method also includes inferring a present activity of a user co-located with the mobile device to be one of the activity classifications based, at least in part, on the determined likelihood functions for the activity classifications at the present epoch.

In an implementation, an apparatus comprises, for each of a plurality of activity classifications, means for determining activity likelihood function values for each of said plurality of activity classifications for two or more past epochs based, at least in part, on signals from one or more sensors of a mobile device. The apparatus also comprises means for combining the activity likelihood function values to determine a likelihood function for an activity classification at a present epoch and means for inferring a present activity of a user co-located with the mobile device to be one of the plurality of activity classifications based, at least in part, on the determined likelihood functions for the activity classifications at the present epoch.

In an implementation, an article comprises, non-transitory storage medium having machine-readable instructions stored thereon which are executable by a processor of a mobile device to, for each of a plurality of activity classifications determine activity likelihood function values for the activity classification for two or more past epochs based, at least in part, on signals from one or more sensors of the mobile device. The processor also combines the activity likelihood function values to determine a likelihood function for the activity classification at a present epoch, and to infer a present activity of a user co-located with the mobile device to be one of the activity classifications based, at least in part, on the determined likelihood functions for the activity classifications at the present epoch.

In an implementation, a mobile device comprises one or more sensors and a processor to, for each of a plurality of activity classifications, determine activity likelihood function values for the activity classification for two or more past epochs based, at least in part on signals from the one or more sensors. The processor may further combine the activity likelihood function values to determine a likelihood function for the activity classification at a present epoch; and infer a present activity of a user co-located with the mobile device to be one of the activity classifications based, at least in part, on the determined likelihood functions for the activity classifications at the present epoch.

BRIEF DESCRIPTION OF DRAWINGS

Non-limiting and non-exhaustive aspects are described with reference to the following figures, wherein like reference numerals refer to like parts throughout the various figures.

DETAILED DESCRIPTION

Figure 1:
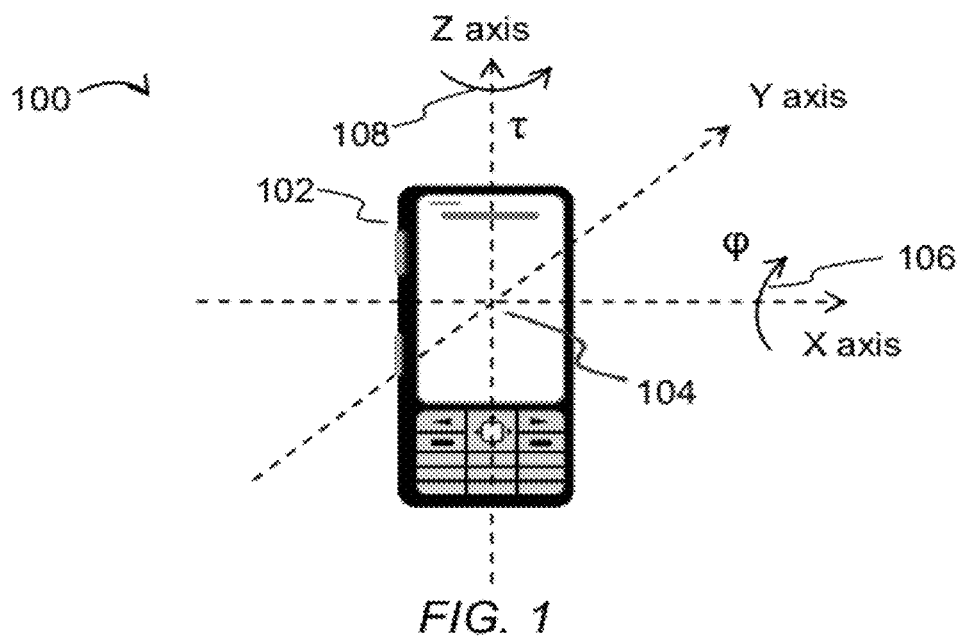
FIG. 1 is an example coordinate system that may be applied to a mobile device according to an implementation.

In a particular implementation, a classifier may infer an activity class of a mobile device user based, at least in part, on signals received from inertial sensors on the mobile device. In particular examples, signals from one or more inertial sensors may be processed to compute or extract "features" that may be indicative or suggestive of a particular activity class. Features computed from inertial sensors may then be applied to an activity estimator to estimate a present activity. Output states of an activity estimator at a given time may be combined with previous output states and filtered to increase a confidence factor of an inference of an activity classification.

Classifier latency may be defined as a total duration of continuous sensor output state that is observed before an inference of a user activity class is generated by the classifier. A higher latency may lead to higher confidence factor in an activity classification as a result of filtering, for example, which may be desirable. However, incurring a delay prior to formulating a decision for an activity class may decrease the value of the decision generated by an activity classifier. For example, if a user transitions from one activity class to another, a classifier may continue to provide an earlier activity classification until a latency period has elapsed. Such latencies may introduce inaccuracies, which may be particularly detrimental in the event that a user's activity state changes at a faster rate than latency. In this event, an activity classifier may completely overlook a short-duration activity.

Particular implementations may accommodate activity classifications having different latency requirements. In one example, an activity classification that supports a calorie-burn counter may allow latency on the order of minutes, since classifier accuracy may presumably be more important than dynamic response. For a calorie-burn counting application, for example, estimating with a high level of confidence that a user exercised continuously for 30 minutes with a one-minute reporting delay may represent an adequate and desirable result. In contrast, estimating, perhaps with a lower level of confidence that a user alternated between running and walking for a total of 15 minutes each with a 1 second reporting delay may not represent a useful accounting. In another example, an activity classification that supports a gaming application may perform satisfactorily with latencies on the order of seconds, or even fractions of a second, but may tolerate activity classifications with lower levels of confidence.

Accordingly, in implementations, an activity classifier may be configured for variable latency settings. Moreover, it may be advantageous for an activity classifier to generate simultaneous classifications having different latencies. In an implementation, if a calorie-burn counting application may be capable of running on a mobile device in parallel with a gaming application, a simple solution to accommodating the diverse latency and accuracy demands of the applications may be to simply execute multiple instantiations of a classifier, with each instantiation operating within a particular latency setting. Implementations described herein may have advantages over such an approach.

In a particular implementation, a classifier may infer that a user co-located with a mobile device is engaged in one of a plurality of activity classifications. In this context, a user may be co-located with a mobile device by holding the mobile device, for example, wearing the mobile device, having the mobile device in his/her pocket, being in immediate contact with the mobile device, just to name a few examples. In an implementation, a "likelihood function" may describe a log-likelihood or other expression derived from or pertaining to a likelihood that a user is engaged in one of a plurality of activity classes. Likelihood function values for one or more of the activity classifications may be determined for sequential epochs by processing signals received from sensors on the mobile device. Likelihood function values inferred over multiple epochs for a particular activity classification may then be combined, filtered, and an activity classification may be inferred based, at least in part, on combined likelihood function values. In particular implementations, likelihood function values may be inferred using various filtering techniques such as Temporal Voting, Maximum Likelihood function, Maximum A-Priori, Finite Impulse Response, and Infinite Impulse Response, just to name a few examples.

In an implementation, a classifier may be configured to adapt a latency to suit particular applications. In an example, a classifier comprising 30-second latency may be configured to switch to estimating an activity class with 10-second latency. In implementations, this may be particularly useful for applications that operate under a confidence requirement, as opposed to a latency requirement.

FIG. 1 is an example coordinate system (100) that may be applied to a mobile device according to an implementation. In FIG. 1, coordinate system 100 may be used, in whole or in part, to facilitate or support an inference of an activity classification in connection with a user of a mobile device, such as a mobile device 102, for example, using accelerometer output signals according to an implementation. It should be understood, however that an accelerometer is but one example of an inertial sensor from which a user activity may be classified and claimed subject matter is not limited in this respect. Examples of inertial sensors may include gyroscopes, magnetometers, piezoelectric devices and so forth. In other implementations, other types of sensors, such as pressure sensors, ambient light sensors, imaging sensors, temperature sensors, just to name a few examples, may produce output signals that may be processed to infer an activity class of a user co-located with a mobile device.

As illustrated, coordinate system 100 may comprise, for example, 3-dimensional Cartesian coordinate system, though claimed subject matter is not so limited. In this illustrated example, motion of mobile device 102 represents, for example, acceleration vibration that may be detected or measured, at least in part, with reference to 3 linear dimensions or axes X, Y, and Z relative to origin 104 of example coordinate system 100. It should be appreciated that example coordinate system 100 may or may not be aligned with the body of mobile device 102. It should also be noted that in certain implementations a non-Cartesian coordinate system, such as a cylindrical or spherical coordinate system, may be used or any other coordinate system that may define mutually orthogonal dimensions.

As also illustrated in FIG. 1, rotational motion of mobile device 102, as the orientation of the device changes about gravity, for example, may be detected or measured, at least in part, with reference to one or two dimensions. In an implementation, rotational motion of mobile device 102 may be detected or measured in terms of coordinates ($\phi$, $\tau$), where phi ($\phi$) represents pitch or rotation about an X-axis, as illustrated generally by an arrow at 106, and tau ($\tau$) represents roll or rotation about a Z-axis, as illustrated generally by an arrow 108. Accordingly, in an implementation, a 3-dimensional accelerometer may detect or measure, at least in part, a level of acceleration vibration as well as a change about gravity with respect to roll or pitch dimensions, for example, thus, providing 5 dimensions of observability (X, Y, Z, $\phi$, $\tau$). However, these are merely examples of various motions that may be detected or measured with reference to example coordinate system 100, and claimed subject matter is not limited to above-described motions or coordinate systems.

Following the above discussion, a 3-dimensional accelerometer may detect or measure accelerations in 3-dimensional space due to various vibrations, for example, in response to activity of a user co-located with the device. Typically, although not necessarily, acceleration vibrations may be associated, for example, with a moving vehicle (e.g., engine, wheels, etc. vibrations, unevenness in a road, etc.), user's walking or running, hand or wrist tremor, aerobic exercise, or other phenomena that may ordinarily exist in mobile settings or environments.

Figure 2:
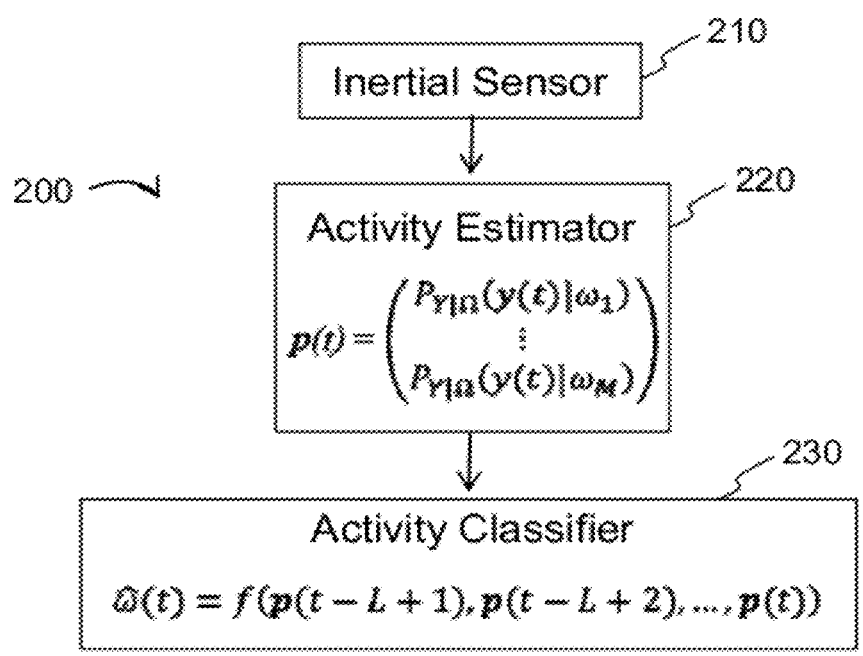
FIG. 2 is a diagram of a process for inferring a user's activity class in a mobile device according to an implementation.

FIG. 2 is a diagram (200) of a process for inferring a user's activity class in a mobile device according to an implementation. In FIG. 2, inertial sensor 210, located on a mobile device, may generate an output "trace" comprising an electrical or other type of signal to activity estimator 220. In an implementation, inertial sensor 210 may comprise an accelerometer that generates one or more output traces representing acceleration of the mobile device projected along various dimensions (e.g. X, Y, Z, $\phi$, $\tau$) of observability.

Output signals from an inertial sensor 210 may be conveyed to activity estimator 220. In an implementation, activity estimator 220 may perform one or more signal processing algorithms to extract features from one or more input signals. In an implementation, activity estimator 220 may implement Cepstral filtering in which speech-processing algorithms are applied to the one or more input signals received from an inertial sensor 210. In particular implementations, one or more features may be extracted from signals from an inertial sensor 210. These include, for example and without limitation:

1. Cepstral Coefficients (CCs);
2. Mel-Frequency Cepstral Coefficients (MFCCs);
3. delta Cepstral Coefficients (dCCs);
4. delta Mel-Frequency Cepstral Coefficients (dMFCCs);
5. accel Cepstral Coefficients (d2CCs);
6. accel Mel-Frequency Cepstral Coefficients (d2MFCCs);
7. Linear Prediction Coefficients (LPCs);
8. delta Linear Prediction coefficients (dLPCs);
9. accel Linear Prediction coefficients (dLPCs);
10. Variance from accelerometer norm; and
11. Accelerometer pitch and roll or other angles associated with accelerometer orientation with respect to gravity.

It should be understood, however, that these are merely examples of features that may be extracted from a signal to characterize a spectral envelope (e.g., for use in inferring an activity class of a user co-located with a mobile device) and claimed subject matter is not limited in this respect.

Regarding extraction of features to characterize a spectral envelope of an inertial sensor signal, CCs or MFCCs may provide a parameterization of a spectral envelope of a waveform, and thus may be useful in distinguishing waveforms arising from different types of motions, such as a user's walk or gait, with a mobile device positioned at different locations on the user. In an implementation, CCs may be used to extract features characterized from an inertial sensor signal in which equal emphasis (i.e. weight) is applied to frequency bands of interest. In other implementations, such as may be used in MFCC feature extraction, lower frequency signals may be emphasized while higher frequency signals are deemphasized.

In an example, a mobile device positioned in a user's hip pocket while the user is walking may result in an accelerometer trace that is different from an accelerometer trace generated in response to the user carrying the mobile device in his or her hand. In this example, a mobile device positioned in the user's pocket may undergo distinct and periodic acceleration in the vertical ($\pm Z$) direction as the user walks but may undergo very little acceleration in the $\pm X$ or $\pm Y$ directions. In contrast, a mobile device positioned in a user's hand while the user walks, may undergo less pronounced periodic acceleration in the vertical ($\pm Z$) direction but may undergo increased acceleration in the $\pm X$ or $\pm Y$ directions, for example.

In an implementation, delta CCs may be used to enhance the performance of CCs by considering velocity (e.g., rate of change with respect to time) of each CC across overlapping windows in addition to static CCs. Accel CCs may further enhance the performance of CCs by additionally considering an acceleration of one or more static CCs across overlapping windows (e.g., rate of change of velocity with respect to time).

In implementations, parameters for delta MFCCs and accel MFCCs may be similarly applied. For example, to apply delta and accel filtering, static MFCCs may be calculated by way of pre-emphasis filtering of frequency bands of interest from the inertial sensor signal. Delta and accel filtering may then be performed on calculated MFCCs to observe velocity and acceleration (as a function of time) of one or more MFCCs.

In implementations, linear prediction coefficients (LPCs) may be used to characterize a spectral envelope if an underlying inertial sensor signal is generated by an all-pole autoregressive process. In an implementation, an LPC may model an inertial sensor output signal at a particular point in time as an approximate linear combination of previous output samples. In an example, an error signal may be added to a set of coefficients that describe the output signal during one or more data windows.

In an implementation, a one-to-one mapping may exist from LPCs to MFCCs. Delta LPCs may enhance the performance of LPCs by additionally considering a velocity (e.g., rate of change as a function of time) of each coefficient across overlapping windows. Accel LPCs may further enhance the performance of LPCs by additionally considering an acceleration of each coefficient across overlapping windows (e.g., rate of change of velocity as a function of time).

In an alternative implementation, other features may be extracted from an inertial sensor signal for use in characterizing an activity of a user collocated with a mobile device (e.g., in lieu of or in combination with a characterization of a spectral envelope). These may include:

1. Pitch;
2. Spectral Entropy;
3. Zero Crossing Rate (ZCR);
4. Spectral Centroid (SC);
5. Bandwidth (BW);
6. Band Energies (BEs);
7. Spectral Flux (SF); and
8. Spectral Roll-off (SR).

In an implementation, pitch, which may define the fundamental frequency of a periodic motion, may be measured from an inertial sensor signal. A measurement of pitch may be useful, for example, in differentiating between or among activities having similar motions that occur at different rates, such as, for example, jogging vs. running, strolling vs. a brisk walk, and so forth.

In an implementation, spectral entropy, which may correspond to a short-duration frequency spectrum of an inertial sensor signal if normalized and viewed as a probability distribution, may be measured. For example, a measurement of spectral entropy may enable parameterization of a degree of periodicity of a signal. In an example, lower spectral entropy, calculated from an accelerometer trace, may indicate that the user is engaged in a periodic activity such as walking, jogging, cycling, and so forth. Higher spectral entropy, on the other hand, may be an indicator that the user is engaged in an aperiodic activity such as manipulating the device or driving an automobile on an uneven road.

In an implementation, a zero crossing rate, which may describe the number of times per second an inertial sensor signal crosses its mean value in a certain time window, may be measured. Measurement of a zero crossing rate may be useful in differentiating between or among motions or device positions that produce inertial sensor signals that fluctuate at different rates, such as walking, which may be indicated by slower fluctuations between positive and negative values vs. running, which may be indicated by more rapid fluctuations between positive and negative values.

In an implementation, a spectral centroid, which may represent a mean frequency of a short-duration frequency spectrum of an inertial sensor signal, may be measured. Subband spectral centroids may found by applying a filterbank to the power spectrum of the inertial sensor signal, and then calculating the first moment (or centroid) for each subband. The signal frequency range may then be partitioned into a number of bins. A corresponding bin for each subband may be determined and incremented by one. Cepstral coefficients may then be determined by computing the discrete cosine transform of a resulting histogram.

In an implementation, a bandwidth, which may be represented as a standard deviation of the short time frequency spectrum of an inertial sensor signal may be measured. In an example, the bandwidth of an inertial sensor signal may be used to complement one or more other measurements, such as those described herein. In an implementation, band energies, which may be descriptive of energies in different frequency bands of a short duration frequency spectrum of an inertial sensor signal, may be measured.

In various implementations, measurements of spectral centroid, bandwidth and/or band energies may be useful, for example, in differentiating between or among motions or device positions that produce inertial sensor signal outputs, which may indicate energy concentrations in different portions of a frequency spectrum (e.g., high frequency activities vs. low frequency activities). In some implementations, these additional measurements, made in conjunction with other measurements may be used to increase a likelihood function of a correct activity detection based on an inertial sensor signal.

In an implementation, spectral flux, which may be the average of the difference between the short time frequency spectra across two consecutive windows of an inertial sensor signal, may be measured. Measurement of spectral flux may be used, for example, in characterizing the speed at which a particular periodic behavior is changing (e.g., in characterizing an aerobic activity in which an activity level may change significantly in a short time).

In an implementation, spectral roll-off, which may be the frequency below which a certain fraction of the signal energy resides, may be measured. In an example, spectral roll-off may be useful in characterizing the shape of a frequency spectrum, which may be useful in determining user activity when combined with other measurements.

As a result of one or more of the above-identified feature-extraction techniques and/or as a result of other signal processing, activity estimator 220 may generate a column vector expressing likelihood functions for various activity classes at one or more epochs. In an implementation, the column vector may be in the form of:

$$p(t) = \begin{pmatrix} P_{(Y|\Omega)(y(t)|\omega_1)} \\ \vdots \\ P_{(Y|\Omega)(y(t)|\omega_M)} \end{pmatrix}$$

In an implementation, activity estimator 220 may generate the column vector p(t) during an end portion of each epoch. In a particular implementation, an epoch may occur at approximately 1-second intervals. However, in other implementations, an epoch may comprise a longer interval, such as approximately 2 seconds, 3 seconds, or more. In other implementations, an epoch may comprise a shorter interval, such as approximately ½ second, ¼ second, and so forth.

In an implementation, p(t) comprises estimates of the likelihood of observing information states given an underlying user activity class (ω), wherein y(t) represents observations in the form of one or more accelerometer traces, for example, from an inertial sensor 210. Accordingly, for example, if $\omega_1$=running, the quantity $P_{Y|\Omega}(y(t)|\omega_1)$ may represent the statistical likelihood that the underlying user activity class is "running." In a similar example, if $\omega_2$=walking, the quantity $P_{Y|\Omega}(y(t)|\omega_2)$ may represent the statistical likelihood that the underlying user activity class is "walking," and so forth. In an implementation, the column vector p(t) indicates estimates of likelihood that the user is engaged in one or more of "M" number of activity classes.

In an implementation, the column vector p(t) may be conveyed to activity classifier 230 at particular intervals, such as once per second. Activity classifier 230 may infer a present activity class by combining and filtering the column vector p(t) as well as historical values for the column vector p(t). Thus, an estimation of a current activity class may be expressed as:

$$\hat{\omega}(t) = f(p(t-L+1), p(t-L+2), \ldots, p(t))$$

In the above expression, activity classifier 230 includes "L" estimates of an activity as expressed by column vector p(t). Accordingly, in an implementation, activity classifier 230 includes latency in calculating an inference of an activity class. Thus, in an example in which activity classifier 230 includes five estimates of an activity prior to generating an activity decision, an inference of an activity classification may be expressed as follows:

$$(t) = f(p(t-4), p(t-3), p(t-2), p(t-1), p(t))$$

Of course, in other implementations, activity classifier 230 includes any number of estimates of an activity prior to generating activity decision. For example, an activity classifier may include as few as two estimates of activity prior to generating an inference of an activity class, or may include dozens or even hundreds or thousands of estimates of an activity prior to generating an inference of an activity class.

Figure 3:
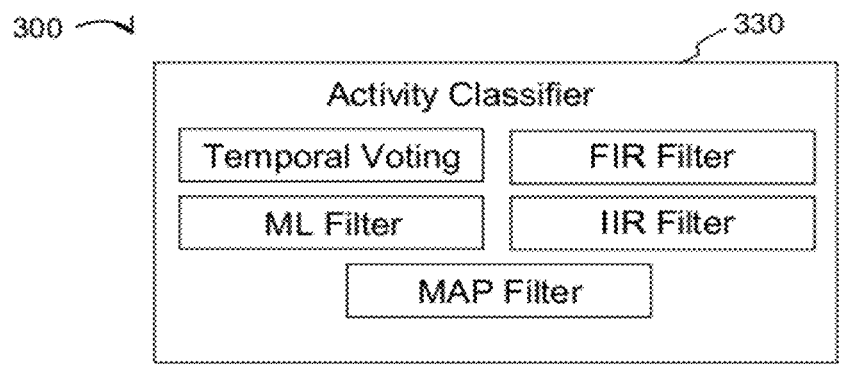
FIG. 3 is a diagram showing additional details of the temporal combiner of FIG. 2.

FIG. 3 is a diagram (300) showing additional details of the temporal combiner of FIG. 2. In FIG. 3, Temporal Voting, Maximum Likelihood Combining, Maximum A Priori combining, Finite Impulse Response filtering, and infinite impulse response filtering represent a small number of techniques by which prior estimates of an activity may be used to generate an activity decision. However, numerous additional techniques may be employed, and claimed subject matter is not limited in this respect.

In an implementation, Temporal Voting may be employed to infer an activity class having a higher frequency of being inferred at past epochs. In Temporal Voting, an inference of an activity class may be given by:

$$\hat{\omega}(t) = \mathrm{argmax}_{\omega_j \in \{\omega_1,\ldots,\omega_M\}}$$

$$\sum_{k=t-L+1}^{t} I\{P_{(Y|\Omega)(y(k)|\omega_j)} \geq P_{(Y|\Omega)(y(k)|\omega_M)}, \text{ for } m = 1, \ldots, M\}$$

In which, $I_x$ comprises an indicator function for the event X, i.e.

$$I_X = \begin{cases} 1 & \text{if } X \text{ occurs} \\ 0 & \text{otherwise} \end{cases}$$

And in which the inferred activity class $\hat{\omega}(t)$ is one of:

activity1, activity2, . . . , activityM

In Temporal Voting, for the "L" column vectors representing current and past estimates of p(t), such as, for example, p(t−L+1), p(t−L+2), . . . , p(t), the "L" vector representing the activity comprising the highest likelihood based, at least in part, on inferences made for past epochs is calculated. For example, for L=5, in the event that 3 estimates of an activity class indicate that the user is, for example, "walking," an activity classifier employing temporal voting may infer that a user's current activity class equals "walking" as well.

In an implementation in which activity classifier 330 comprises Maximum Likelihood filtering, an assumption is made that observations {Y(t−L+1), Y(t−L+2), . . . , Y(t)}, comprise jointly independent samples of observed information state y(t). In an implementation, {Y(t−L+1), Y(t−L+2), . . . , Y(t)} may represent features extracted from one or more output signals from an inertial sensor at various epochs using speech processing or other signal processing techniques. In an implementation, an inference of an activity class may result from applying a moving-average filter to log-likelihoods of estimations of an activity class:

$$\hat{\omega}(t) = \mathrm{argmax}_{\omega_j \in \{\omega_1,\ldots,\omega_M\}} \sum_{k=t-L+1}^{t} \log P_{(Y|\Omega)(y(k)|\omega_j)}$$

Under a similar, at least in part, assumption that observations {Y(t−L+1), Y(t−L+2), . . . , Y(t)} comprise jointly independent samples of observed information state y(t), an implementation of FIG. 3 may comprise a Maximum A Priori (MAP) filter that filters log-likelihoods of an activity class:

$$\hat{\omega}(t) = \mathrm{argmax}_{\omega_j \in \{\omega_1,\ldots,\omega_M\}} \left( \log P_\Omega(\omega_j) + \sum_{k=t-L+1}^{t} \log P_{(Y|\Omega)(y(k)|\omega_j)} \right);$$

In the above expression, $P_\Omega(\omega_1), \ldots, P_\Omega(\omega_M)$ represents prior likelihoods for "M" activity classes. In an example, if a set of activity classes comprises walking ($\omega_1$) and stationary ($\omega_2$), and walking occurs with a 10% likelihood while stationary occurs with a 90% likelihood, then one possible setting may be $P_\Omega(\omega_1)=0.1$ and $P_\Omega(\omega_2)=0.9$.

In an implementation, activity classifier 330 may implement Finite Impulse Response filtering. In an implementation, the log-likelihoods of estimations of activity classes are first filtered. The Finite Impulse Response filtering solution is given by:

$$\hat{\omega}(t) = \mathrm{argmax}_{\omega_j \in \{\omega_1,\ldots,\omega_M\}} \sum_{k=t-L+1}^{t} a(k)x(k)$$

$$\hat{\omega}(t) = \mathrm{argmax}_{\omega_j \in \{\omega_1,\ldots,\omega_M\}} \sum_{k=t-L+1}^{t} a(k)x(k)$$

In which, $x(k) = \log P_{y|\Omega}(y)k)|\omega_j)$.

In the above expression, the Finite Impulse Response coefficients a(t−L+1), a(t−L+2), . . . , a(t) may be arbitrarily chosen to bias an activity class decision to more recent or to less recent activity estimations. In an implementation, biasing Finite Impulse Response coefficients towards more recent inferences, may enable activity classifier 330 to adapt from performing higher latency inferences to lower latency inferences.

In an implementation, activity classifier 330 may implement Infinite Impulse Response filtering. For example, an activity class may be inferred by way of a filtering solution of:

$$\hat{\omega}(t) = \mathrm{argmax}_{\omega_j \in \{\omega_1,\ldots,\omega_M\}} q(t)$$

In which:

$$q(t) = \sum_{k=t-L+1}^{t-1} a(k)x(k) + \sum_{k=t-L+1}^{t-1} b(k)q(k)$$

In the above expression, the Infinite Impulse Response coefficients b(t−L+1), b(t−L+2), . . . , b(t−1) may be chosen in a manner that preserves the stability of activity classifier 330.

Figure 4:
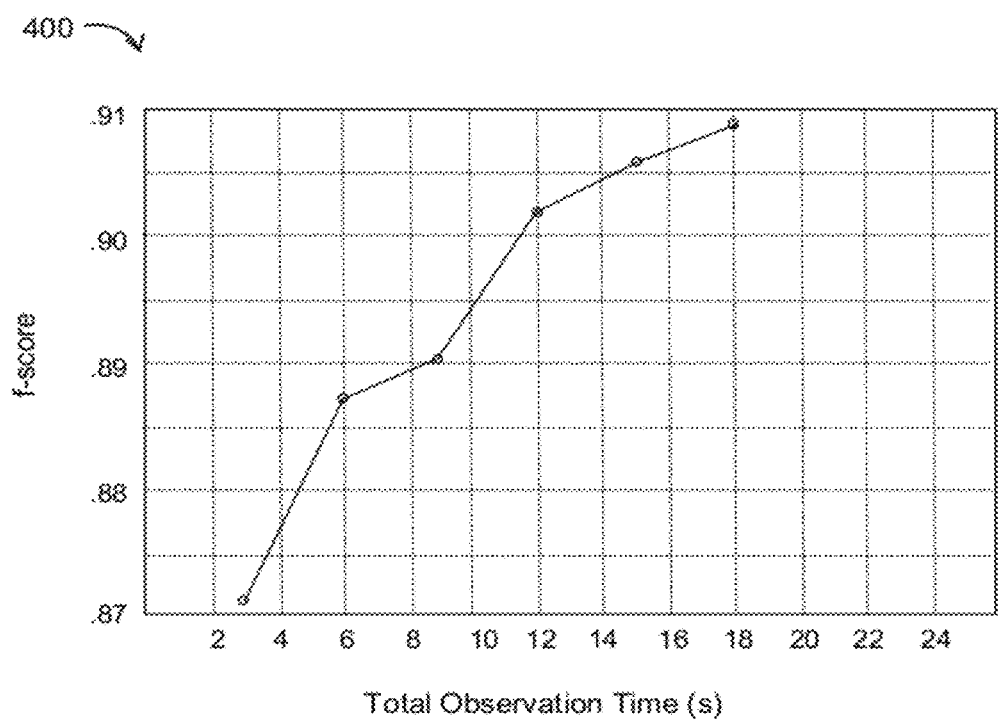
FIG. 4 is a graph showing a measure of confidence as a function of observation time for a maximum likelihood function combiner according to an implementation.

FIG. 4 is a graph (400) showing a measure of confidence as a function of observation time for a Maximum Likelihood filter according to an implementation. In FIG. 4, "f-score" may represent a confidence level of a classification from an activity classifier that generates an activity classification at 3-second epochs. After an initial 3-second epoch, an activity class may be inferred with an approximately 87% level of confidence. After an additional 3-second epoch, corresponding to an observation time of six seconds, an activity class may be inferred with nearly an 89% level of confidence. After an observation time of approximately 9 seconds, an activity class may be inferred with better than an 89% level of confidence. After an observation time of approximately 12 seconds, an activity class may be inferred with better than a 90% level of confidence. After an observation time of approximately 15 seconds, an activity class may be inferred with better than a 90.5% level of confidence. After an observation time of approximately 18 seconds, an activity class may be inferred with nearly a 91% level of confidence.

In an implementation, by way of temporal combining of activity estimations, a mobile device may be configured to execute a single instantiation of an activity classifier having lower latency and lower accuracy. However, when classifier output states are combined by way of one or more filtering techniques described herein, a higher latency, higher accuracy inference of an activity class may result. Inferences of an activity class may be scalable so that combining a desired number of output states environment 500, processes, or methods, as described herein, may be implemented using various hardware, firmware, or any combination thereof along with software.

Computing environment 500 may include, for example, a mobile device 502, which may be communicatively coupled to any number of other devices, mobile or otherwise, via a suitable communications network, such as a cellular telephone network, the Internet, mobile ad-hoc network, wireless sensor network, or the like. In an implementation, mobile device 502 may be representative of any electronic device, appliance, or machine that may be capable of exchanging information over any suitable communications network. For example, mobile device 502 may include one or more computing devices or platforms associated with, for example, cellular telephones, satellite telephones, smart telephones, personal digital assistants (PDAs), laptop computers, personal entertainment systems, e-book readers, tablet personal computers (PC), personal audio or video devices, personal navigation devices, or the like. In certain example implementations, mobile device 502 may take the form of one or more integrated circuits, circuit boards, or the like that may be operatively enabled for use in another device. Although not shown, optionally or alternatively, there may be additional devices, mobile or otherwise, communicatively coupled to mobile device 502 to facilitate or otherwise support 1 or more processes associated with computing environment 500. Thus, unless stated otherwise, to simplify discussion, various functionalities, elements, components, etc. are described below with reference to mobile device 502 may also be applicable to other devices not shown so as to support one or more processes associated with example computing environment 500.

Computing environment 500 may include, for example, various computing or communication resources capable of providing position or location information with regard to a mobile device 502 based, at least in part, on one or more wireless signals associated with a positioning system, location-based service, or the like. Although not shown, in certain example implementations, mobile device 502 may include, for example, a location-aware or tracking unit capable of acquiring or providing all or part of orientation, position information (e.g., via trilateration, heat map signature matching, etc.), etc. Such information may be provided in support of one or more processes in response to user instructions, motion-controlled or otherwise, which may be stored in memory 504, for example, along with other suitable or desired information, such as one or more threshold values, or the like.

Memory 504 may represent any suitable or desired information storage medium. For example, memory 504 may include a primary memory 506 and a secondary memory 508. Primary memory 506 may include, for example, a random access memory, read only memory, etc. While illustrated in this example as being separate from a processing unit 510, it should be appreciated that all or part of primary memory 506 may be provided within or otherwise co-located/coupled with processing unit 510. Secondary memory 508 may include, for example, the same or similar type of memory as primary memory or one or more information storage devices or systems, such as, for example, a disk drive, an optical disc drive, a tape drive, a solid state memory drive, etc. In certain implementations, secondary memory 508 may be operatively receptive of, or otherwise enabled to be coupled to, a non-transitory computer-readable medium 512.

Computer-readable medium 512 may include, for example, any medium that can store or provide access to information, code or instructions (e.g., an article of manufacture, etc.) for one or more devices associated with computing environment 500. For example, computer-readable medium 512 may be provided or accessed by processing unit 510. As such, in certain example implementations, the methods or apparatuses may take the form, in whole or part, of a computer-readable medium that may include computer-implementable instructions stored thereon, which, if executed by at least one processing unit or other like circuitry, may enable processing unit 510 or the other like circuitry to perform all or portions of a location determination processes, sensor-based or sensor-supported measurements (e.g., acceleration, deceleration, orientation, tilt, rotation, etc.), extraction/computation of features from inertial sensor signals, classifying an activity co-located with a user of mobile device, or any like processes to facilitate or otherwise support rest detection of mobile device 502. In certain example implementations, processing unit 510 may be capable of performing or supporting other functions, such as communications, gaming, or the like.

Processing unit 510 may be implemented in hardware or a combination of hardware and software. Processing unit 510 may be representative of one or more circuits capable of performing at least a portion of information computing technique or process. By way of example but not limitation, processing unit 510 may include one or more processors, controllers, microprocessors, microcontrollers, application specific integrated circuits, digital signal processors, programmable logic devices, field programmable gate arrays, or the like, or any combination thereof.

Mobile device 502 may include various components or circuitry, such as, for example, one or more accelerometers 513, or various other sensor(s) 514, such as a magnetic compass, a gyroscope, a video sensor, a gravitometer, etc. to facilitate or otherwise support one or more processes associated with computing environment 500. For example, such sensors may provide analog or digital signals to processing unit 510. Although not shown, it should be noted that mobile device 502 may include an analog-to-digital converter (ADC) for digitizing analog signals from one or more sensors. Optionally or alternatively, such sensors may include a designated (e.g., an internal, etc.) ADC(s) to digitize respective output signals, although claimed subject matter is not so limited.

Although not shown, mobile device 502 may also include a memory or information buffer to collect suitable or desired information, such as, for example, accelerometer measurement information (e.g., accelerometer traces), as previously mentioned. Mobile device may also include a power source, for example, to provide power to some or all of the components or circuitry of mobile device 502. A power source may be a portable power source, such as a battery, for example, or may comprise a fixed power source, such as an outlet (e.g. in a house, electric charging station, car, etc.). It should be appreciated that a power source may be integrated into (e.g., built-in, etc.) or otherwise supported by (e.g., stand-alone, etc.) mobile device 502.

Mobile device 502 may include one or more connection bus 516 (e.g., buses, lines, conductors, optic fibers, etc.) to operatively couple various circuits together, and a user interface 518 (e.g., display, touch screen, keypad, buttons, knobs, microphone, speaker, trackball, data port, etc.) to receive user input, facilitate or support sensor-related signal measurements, or provide information to a user. Mobile device 502 may further include a communication interface 520 (e.g., wireless transmitter or receiver, modem, antenna, etc.) to allow for communication with one or more other devices or systems over one or more suitable communications networks, as was indicated.

Figure 5:
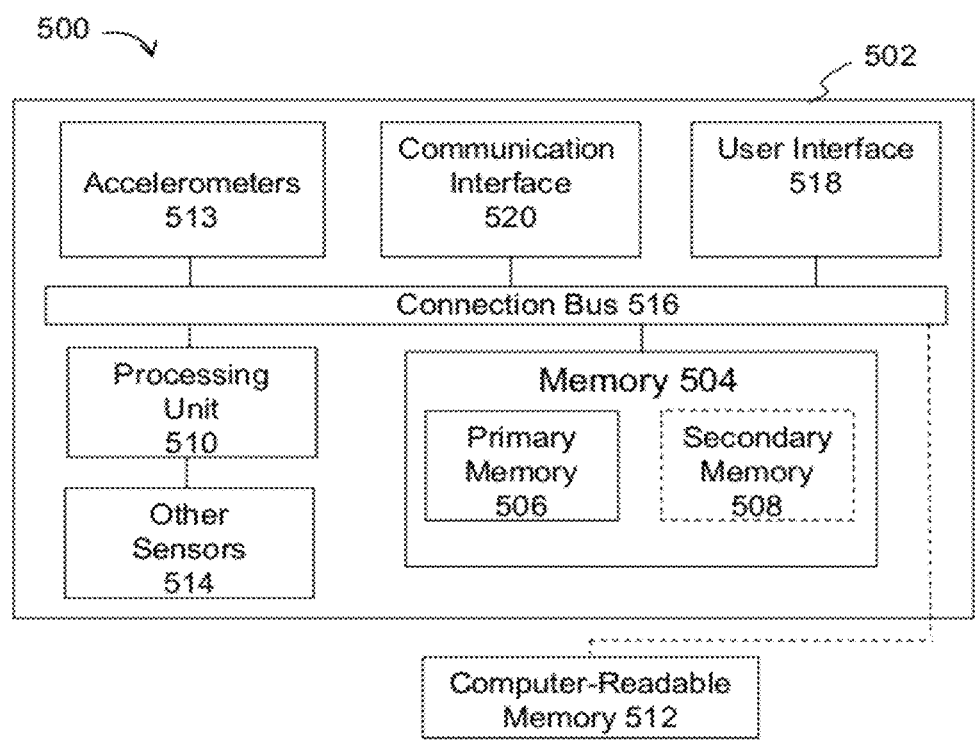
FIG. 5 is a schematic diagram illustrating an example computing environment associated with a mobile device according to an implementation.
Figure 6:
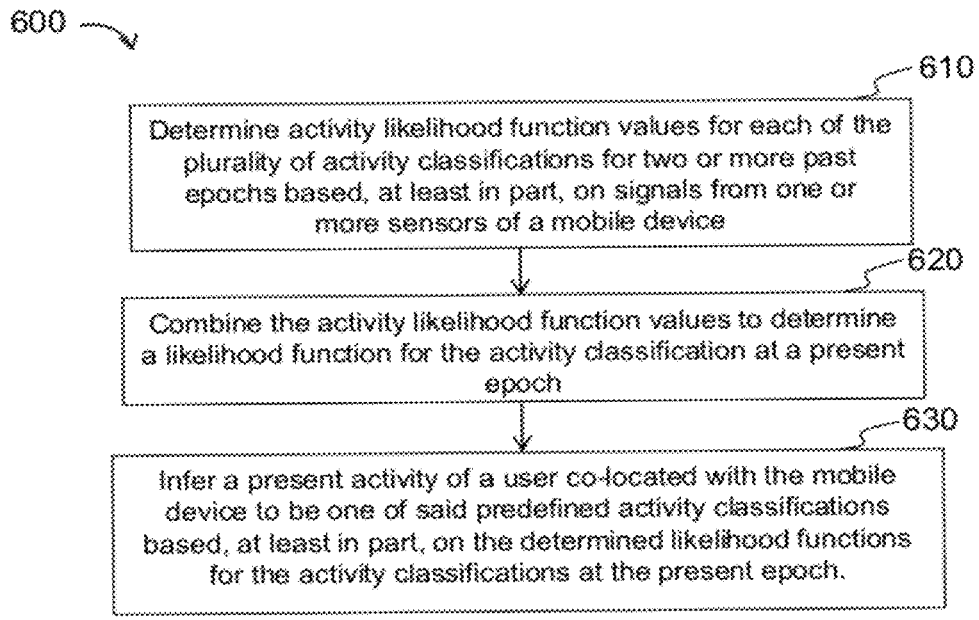
FIG. 6 is a flowchart illustrating a process of classifying user activity using temporal combining according to an implementation.

FIG. 6 is a flowchart (600) illustrating a process of classifying user activity using temporal combining according to an implementation. Although the embodiment of FIG. 5 may be suitable for performing the method of FIG. 6, nothing prevents performing the method using alternative arrangements of structures and components. The method of FIG. 6 begins at block 610, which includes, for each of the plurality of activity classifications, determining activity likelihood function values for each of the plurality of activity classifications for two or more past epochs based, at least in part, on signals from one or more sensors of a mobile device. Block 620 includes combining the activity likelihood function values to determine a likelihood function for the activity classification at a present epoch. The method continues at block 630, which includes inferring a present activity of a user co-located with the mobile device to be one of the activity classifications based, at least in part, on determined likelihood functions for the activity classifications at the present epoch.

Methodologies described herein may be implemented by various means depending upon applications according to particular features or examples. For example, such methodologies may be implemented in hardware, firmware, software, discrete/fixed logic circuitry, any combination thereof, and so forth. In a hardware or logic circuitry implementation, for example, a processing unit may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, electronic devices, other devices or units designed to perform the functions described herein, or combinations thereof, just to name a few examples.

For a firmware or software implementation, the methodologies may be implemented with modules (e.g., procedures, functions, etc.) having instructions that perform the functions described herein. Any machine-readable medium tangibly embodying instructions may be used in implementing the methodologies described herein. For example, software codes may be stored in a memory and executed by a processor. Memory may be implemented within the processor or external to the processor. As used herein the term "memory" refers to any type of long term, short term, volatile, nonvolatile, or other memory and is not to be limited to any particular type of memory or number of memories, or type of media upon which memory is stored. In at least some implementations, one or more portions of the herein described storage media may store signals representative of data or information as expressed by a particular state of the storage media. For example, an electronic signal representative of data or information may be "stored" in a portion of the storage media (e.g., memory) by affecting or changing the state of such portions of the storage media to represent data or information as binary information (e.g., ones and zeros). As such, in a particular implementation, such a change of state of the portion of the storage media to store a signal representative of data or information constitutes a transformation of storage media to a different state or thing.

As was indicated, in one or more example implementations, the functions described may be implemented in hardware, software, firmware, discrete/fixed logic circuitry, some combination thereof, and so forth. If implemented in software, the functions may be stored on a physical computer-readable medium as one or more instructions or code. Computer-readable media include physical computer storage media. A storage medium may be any available physical medium that can be accessed by a computer. By way of example, and not limitation, such computer-readable media can comprise RAM, ROM, EEPROM, CD-ROM or other optical disc storage, magnetic disk storage or other magnetic storage devices, or any other medium that can be used to store desired program code in the form of instructions or data structures and that can be accessed by a computer or processor thereof. Disk and disc, as used herein, includes compact disc (CD), laser disc, optical disc, digital versatile disc (DVD), floppy disk and blue-ray disc where disks usually reproduce data magnetically, while discs reproduce data optically with lasers.

As discussed above, a mobile device may be capable of communicating with one or more other devices via wireless transmission or receipt of information over various communications networks using one or more wireless communication techniques. Here, for example, wireless communication techniques may be implemented using a wireless wide area network (WWAN), a wireless local area network (WLAN), a wireless personal area network (WPAN), or the like. The term "network" and "system" may be used interchangeably herein. A WWAN may be a Code Division Multiple Access (CDMA) network, a Time Division Multiple Access (TDMA) network, a Frequency Division Multiple Access (FDMA) network, an Orthogonal Frequency Division Multiple Access (OFDMA) network, a Single-Carrier Frequency Division Multiple Access (SC-FDMA) network, a Long Term Evolution (LTE) network, a WiMAX (IEEE 802.16) network, and so on. A CDMA network may implement one or more radio access technologies (RATs) such as cdma2000, Wideband-CDMA (WCDMA), Time Division Synchronous Code Division Multiple Access (TD-SCDMA), to name just a few radio technologies. Here, cdma2000 may include technologies implemented according to IS-95, IS-2000, and IS-856 standards. A TDMA network may implement Global System for Mobile Communications (GSM), Digital Advanced Mobile Phone System (D-AMPS), or some other RAT. GSM and W-CDMA are described in documents from a consortium named "3rd Generation Partnership Project" (3GPP). Cdma2000 is described in documents from a consortium named "3rd Generation Partnership Project 2" (3GPP2). 3GPP and 3GPP2 documents are publicly available. A WLAN may include an IEEE 802.11x network, and a WPAN may include a Bluetooth network, an IEEE 802.15x, or some other type of network, for example. The techniques may also be implemented in conjunction with any combination of WWAN, WLAN, or WPAN. Wireless communication networks may include so-called next generation technologies (e.g., "4G"), such as, for example, Long Term Evolution (LTE), Advanced LTE, WiMAX, Ultra Mobile Broadband (UMB), or the like.

In one particular implementation, a mobile device may, for example, be capable of communicating with one or more femtocells facilitating or supporting communications with the mobile device for the purpose of estimating its location, orientation, velocity, acceleration, or the like. As used herein, "femtocell" may refer to one or more smaller-size cellular base stations that may be enabled to connect to a service provider's network, for example, via broadband, such as, for example, a Digital Subscriber Line (DSL) or cable. Typically, although not necessarily, a femtocell may utilize or otherwise be compatible with various types of communication technology such as, for example, Universal Mobile Telecommunications System (UTMS), Long Term Evolution (LTE), Evolution-Data Optimized or Evolution-Data only (EV-DO), GSM, Worldwide Interoperability for Microwave Access (WiMAX), Code division multiple access (CDMA)-2000, or Time Division Synchronous Code Division Multiple Access (TD-SCDMA), to name just a few examples among many possible. In certain implementations, a femtocell may comprise integrated WiFi, for example. However, such details relating to femtocells are merely examples, and claimed subject matter is not so limited.

Also, computer-readable code or instructions may be transmitted via signals over physical transmission media from a transmitter to a receiver (e.g., via electrical digital signals). For example, software may be transmitted from a website, server, or other remote source using a coaxial cable, fiber optic cable, twisted pair, digital subscriber line (DSL), or physical components of wireless technologies such as infrared, radio, and microwave. Combinations of the above may also be included within the scope of physical transmission media. Such computer instructions or data may be transmitted in portions (e.g., first and second portions) at different times (e.g., at first and second times). Some portions of this Detailed Description are presented in terms of algorithms or symbolic representations of operations on binary digital signals stored within a memory of a specific apparatus or special purpose computing device or platform. In the context of this particular Specification, the term specific apparatus or the like includes a general-purpose computer once it is programmed to perform particular functions pursuant to instructions from program software. Algorithmic descriptions or symbolic representations are examples of techniques used by those of ordinary skill in the signal processing or related arts to convey the substance of their work to others skilled in the art. An algorithm is here, and generally, considered to be a self-consistent sequence of operations or similar signal processing leading to a desired result. In this context, operations or processing involve physical manipulation of physical quantities. Typically, although not necessarily, such quantities may take the form of electrical or magnetic signals capable of being stored, transferred, combined, compared, or otherwise manipulated.

It has proven convenient at times, principally for reasons of common usage, to refer to such signals as bits, information, values, elements, symbols, characters, variables, terms, numbers, numerals, or the like. It should be understood, however, that all of these or similar terms are to be associated with appropriate physical quantities and are merely convenient labels. Unless specifically stated otherwise, as is apparent from the discussion above, it is appreciated that throughout this Specification discussions utilizing terms such as "processing," "computing," "calculating," "determining," "ascertaining," "identifying," "associating," "measuring," "performing," or the like refer to actions or processes of a specific apparatus, such as a special purpose computer or a similar special purpose electronic computing device. In the context of this Specification, therefore, a special purpose computer or a similar special purpose electronic computing device is capable of manipulating or transforming signals, typically represented as physical electronic, electrical, or magnetic quantities within memories, registers, or other information storage devices, transmission devices, or display devices of the special purpose computer or similar special purpose electronic computing device.

Terms, "and" and "or" as used herein, may include a variety of meanings that also is expected to depend at least in part upon the context in which such terms are used. Typically, "or" if used to associate a list, such as A, B, or C, is intended to mean A, B, and C, here used in the inclusive sense, as well as A, B, or C, here used in the exclusive sense. In addition, the term "one or more" as used herein may be used to describe any feature, structure, or characteristic in the singular or may be used to describe some combination of features, structures or characteristics. However, it should be noted that this is merely an illustrative example and claimed subject matter is not limited to this example.

While certain example techniques have been described and shown herein using various methods or systems, it should be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter not be limited to particular examples disclosed, but that such claimed subject matter may also include all implementations falling within the scope of the appended claims, and equivalents thereof.

What is claimed is:

1. A method comprising:
   for each of a plurality of activity classifications:
   determining activity likelihood function values for each of said plurality of activity classifications for two or more past epochs from simultaneous classifiers based, at least in part, on signals from one or more sensors of a mobile device;
   combining said activity likelihood function values to determine a likelihood function for an activity classification at a present epoch;
   inferring a present activity of a user co-located with said mobile device to be one of the activity classifications based, at least in part, on said determined likelihood function for said activity classification at said present epoch.

2. The method of claim 1, wherein said activity likelihood function values comprise log-likelihoods.

3. The method of claim 1, wherein inferring said present activity comprises filtering said combined likelihood function values by way of Temporal Voting.

4. The method of claim 1, wherein inferring said present activity comprises filtering said combined likelihood function values by way of Maximum Likelihood filtering.

5. The method of claim 1, wherein inferring said present activity comprises filtering said combined likelihood function values by way of Maximum A Priori filtering.

6. The method of claim 1, wherein inferring said present activity comprises filtering said combined likelihood function values by way of a Finite Impulse Response filter.

7. The method of claim 1, wherein inferring said present activity comprises filtering said combined likelihood function values by way of an Infinite Impulse Response filter.

8. The method of claim 1, wherein each of said plurality of activity classifications is mutually exclusive.

9. The method of claim 1, wherein said one or more sensors comprises at least one accelerometer.

10. The method of claim 9, wherein said one or more sensors comprises said at least one accelerometer in each of three linear dimensions.

11. The method of claim 1, wherein said combining said activity likelihood function values to determine said likelihood function for said activity classification at said present epoch further comprises identifying said activity classification having a highest likelihood function most frequently over said two or more past epochs.

12. An apparatus comprising:
   for each of a plurality of activity classifications:
   means for determining activity likelihood function values for each of said plurality of activity classifications for two or more past epochs from simultaneous classifiers based, at least in part, on signals from one or more sensors of a mobile device; and
   means for combining said activity likelihood function values to determine a likelihood function for an activity classification at a present epoch; and
   means for inferring a present activity of a user co-located with said mobile device to be one of said plurality of activity classifications based, at least in part, on said determined likelihood function for said activity classification at said present epoch.

13. The apparatus of claim 12, wherein said means for inferring said present activity comprises at least one of Temporal Voting, Maximum Likelihood filtering, Maximum A Priori filtering, Finite Impulse Response filtering, and Infinite Impulse Response filtering.

14. The apparatus of claim 12, wherein said one or more sensors comprises at least one accelerometer in each of three linear dimensions.

15. An article comprising:
non-transitory storage medium having machine-readable instructions stored thereon which are executable by a processor of a mobile device to:
for each of a plurality of activity classifications:
determine activity likelihood function values for an activity classification for two or more past epochs from simultaneous classifiers based, at least in part, on signals from one or more sensors of said mobile device; and
combine said activity likelihood function values to determine a likelihood function for said activity classification at a present epoch; and
infer a present activity of a user co-located with said mobile device to be one of said activity classifications based, at least in part, on said determined likelihood function value for said activity classification at said present epoch.

16. The article of claim 15, wherein said non-transitory storage medium further includes machine-readable instructions stored thereon which are executable by said processor of said mobile device to infer said present activity of said user co-located with said mobile device using Temporal Voting.

17. The article of claim 15, wherein said non-transitory storage medium further includes machine-readable instructions stored thereon which are executable by said processor of said mobile device to infer said present activity of said user co-located with said mobile device using Maximum Likelihood filtering.

18. The article of claim 15, wherein said non-transitory storage medium further includes machine-readable instructions stored thereon which are executable by said processor of said mobile device to infer said present activity of said user co-located with said mobile device using Maximum A Priori filtering.

19. The article of claim 15, wherein said non-transitory storage medium further includes machine-readable instructions stored thereon which are executable by said processor of said mobile device to infer said present activity of said user co-located with said mobile device using Finite Impulse Response filtering.

20. The article of claim 15, wherein said non-transitory storage medium further includes machine-readable instructions stored thereon which are executable by said processor of said mobile device to infer said present activity of said user co-located with said mobile device using Infinite Impulse Response filtering.

21. A mobile device comprising:
one or more sensors; and
a processor to:
for each of a plurality of activity classifications:
determine activity likelihood function values for said plurality of activity classifications for two or more past epochs from simultaneous classifiers based, at least in part, on signals from said one or more sensors;
combine said activity likelihood function values to determine a likelihood function for an activity classification at a present epoch; and
infer a present activity of a user co-located with said mobile device to be one of said activity classifications based, at least in part, on said determined likelihood function for said activity classification at said present epoch.

22. The mobile device of claim 21, wherein said signals from said one or more sensors comprise accelerometer traces in three linear dimensions.

23. The mobile device of claim 21, wherein said processor to infer said present activity of said user co-located with said mobile device implements Temporal Voting.

24. The mobile device of claim 21, wherein said processor to infer said present activity of said user co-located with said mobile device implements Maximum Likelihood filtering.

25. The mobile device of claim 21, wherein said processor to infer said present activity of said user co-located with said mobile device implements Maximum A Priori filtering.

26. The mobile device of claim 21, wherein said processor to infer said present activity of said user co-located with said mobile device implements Finite Impulse Response filtering.

27. The mobile device of claim 21, wherein said processor to infer said present activity of said user co-located with said mobile device implements Infinite Impulse Response filtering.

* * * * *